United States Patent [19]

Sewell, Jr.

[11] Patent Number: 5,359,995
[45] Date of Patent: Nov. 1, 1994

[54] METHOD OF USING AN INFLATABLE LAPAROSCOPIC RETRACTOR

[76] Inventor: Frank Sewell, Jr., 1413 N. Elm, Henderson, Ky. 42420

[21] Appl. No.: 831,155

[22] Filed: Feb. 5, 1992

Related U.S. Application Data

[63] Continuation-in-part of Ser. No. 650,049, Feb. 4, 1991, abandoned.

[51] Int. Cl.$^5$ .............................................. A61B 17/02
[52] U.S. Cl. ..................................... 128/20; 606/192; 128/898
[58] Field of Search ................. 128/20, 3, 898; 606/192, 191; 604/98, 167, 165, 104

[56] References Cited

U.S. PATENT DOCUMENTS

| | | | |
|---|---|---|---|
| 2,701,559 | 2/1955 | Cooper | 128/2 |
| 3,863,639 | 2/1975 | Kleaveland | 128/303 R |
| 4,207,872 | 6/1980 | Meiri et al. | 128/4 |
| 4,219,026 | 8/1980 | Layton | 606/192 |
| 4,312,353 | 1/1982 | Schahabian | 128/344 |
| 4,517,979 | 5/1985 | Pecenka | 604/99 |
| 4,638,803 | 1/1987 | Rand | 128/325 |
| 4,714,074 | 12/1987 | Rey et al. | 128/1.1 |
| 4,723,547 | 2/1988 | Kullas et al. | 606/185 |
| 4,800,901 | 1/1989 | Rosenberg | 128/899 |
| 4,889,107 | 12/1989 | Kaufman | 128/20 |
| 4,899,747 | 2/1990 | Garren et al. | 606/192 |
| 4,990,139 | 2/1991 | Jang | 606/192 |
| 5,002,556 | 3/1991 | Ishida et al. | 606/192 |
| 5,036,868 | 8/1991 | Berggren et al. | 128/898 |
| 5,041,092 | 8/1991 | Barwick | 604/104 |
| 5,064,434 | 11/1991 | Haber | 623/11 |
| 5,116,305 | 5/1992 | Milder et al. | 606/192 |
| 5,163,949 | 11/1992 | Bonutti | 606/192 |
| 5,176,692 | 1/1993 | Wilk et al. | 606/191 X |
| 5,195,507 | 3/1993 | Bilweis | 128/20 |

OTHER PUBLICATIONS

Walter Lorenz Retractors Brochure showing Richardson Retractors, Walter Lorenz Surgical Instruments, Inc., Jacksonville, Fla.

Primary Examiner—Richard J. Apley
Assistant Examiner—Donna L. Maraglio
Attorney, Agent, or Firm—Ice Miller Donadio & Ryan

[57] ABSTRACT

A laparoscopic surgical retractor has a substantially rigid insufflation tube insertable through a laparoscopic trocar, a valve for introducing fluid or gas into one end of the tube, and an elastic skin enclosing a variable volume cavity connected to the opposite end. During laparoscopic surgery, the retractor is inserted into a body cavity through a laparoscopic trocar, and then the elastic skin is inflated through the insufflation tube. The elastic skin is positioned against the tissue to be retracted. The retractor may either be held in place by the laparoscopic trocar, or else fully inserted into a body cavity and held in place by its own weight. Following the surgical procedure, the elastic skin is deflated and the device removed through the trocar.

3 Claims, 7 Drawing Sheets

§ 1

METHOD OF USING AN INFLATABLE LAPAROSCOPIC RETRACTOR

CROSS REFERENCE TO RELATED APPLICATIONS

This is a continuation-in-part of application Ser. No. 07/650,049 filed Feb. 4, 1991, now abandoned.

FIELD OF THE INVENTION

This invention relates to a surgical retractors, and in particular, to a surgical retractor that is usable during laparoscopic surgery.

BACKGROUND OF THE INVENTION

During internal surgery it is often necessary to alter the position of various organs or tissues to provide access to the tissues which are the subject of the surgery. It is also necessary to hold the organs or tissues which have been so moved in a stable position during the surgery so that movement thereof will not interfere with the work of the surgeon or surgical assistants.

Devices which move and hold viscera for this purpose are referred to as surgical retractors because of their function of retracting the interfering tissues from the operating field. A number of such devices exist for use where a relatively large incision has been made in the subject's body. Often these devices have broad surfaces to distribute the forces they exert on the viscera over larger areas and thus minimize trauma. One such retractor is shown in U.S. Pat. 4,889,107. Another such retractor is the Richardson Retractor manufactured by Walter Lorenz Surgical Instruments, Inc. of Jacksonville, Fla. Both these devices are inserted through large incisions which makes them unsuitable for laparoscopic surgery.

In laparoscopic surgery only small incisions are made, thereby minimizing trauma and post-operative pain. An endoscope is used to illuminate the internal organs and tissues and provide the surgeon with visual feedback which may be magnified and displayed optically and electronically. Surgical instruments are introduced through flexible tubes, trocars or the operating sheath of an endoscope, which may be only one (1) centimeter in diameter, and are remotely manipulated by the surgeon.

Conventional retractors are too large to enter the body through the small incisions made during laparoscopic surgery and in some cases may be disproportionate in size to the tissues to be retracted. Accordingly it is common during laparoscopic surgery to retract tissues using very small forceps to push or pull the tissues, which increases the risk of injury or trauma. In some instances, a camera held in place by trocar may be used to push tissue or organs such as the transverse colon away from the surgical site during laparoscopic surgery. However, the camera tends to get hot and may damage or even perforate the tissue with which the camera is in contact. Thus, it is desireable to develop a laparoscopic retractor which does not damage the retracted tissue.

Inflatable or collapsible devices or balloons have been used in surgery or body treatment for various purposes. A surgical retractor for conventional surgery which collapses for ease of removal just before final closure is shown in U.S. Pat. 3,863,639. Balloons have also been inserted in the body for a variety of large scale applications such as opening passageways, as seen in U.S. Pat. Nos. 4,312,353; 4,714,074; 4,800,901 and 4,899,747. One inflatable device for use in propelling an endoscope through a body passage is shown in U.S. Pat. 4,207,872.

OBJECTS OF THE INVENTION

Accordingly, it is one object of the present invention to provide a surgical retractor that can be used during laparoscopic surgery.

It is another object of the present invention to provide a laparoscopic retractor that may be easily adjusted in size to match the tissue to be retracted.

It is another object of the present invention to provide a laparoscopic retractor that has a large surface area to retract tissue to minimize the risk of trauma to the retracted tissue.

It is another object of the present invention to provide a laparoscopic retractor that can be completely inserted through a laparoscopic trocar and into a body cavity so that multiple retractors may be introduced to the body cavity through a single laparoscopic trocar.

It is another object of the present invention to provide a laparoscopic retractor which does not damage or perforate the tissue to be retracted.

It still is another object of the present invention to provide a method for retracting tissue during laparoscopic surgery which minimizes the number of incisions required for retraction devices.

SUMMARY OF THE INVENTION

A laparoscopic surgical retractor has a substantially rigid insufflation tube insertable through a laparoscopic trocar, a valve for introducing fluid or gas into one end of the tube, and an elastic skin enclosing a variable volume cavity connected to the opposite end. During laparoscopic surgery, the retractor is inserted into a body cavity through a laparoscopic trocar, and then the elastic skin is inflated through the insufflation tube. The elastic skin is positioned against the tissue to be retracted. The retractor may either be held in place by a laparoscopic trocar, or else fully inserted into a body cavity and held in place by its own weight. Following the surgical procedure, the elastic skin is deflated and the device removed through the trocar.

DETAILED DESCRIPTION

Figure 1:
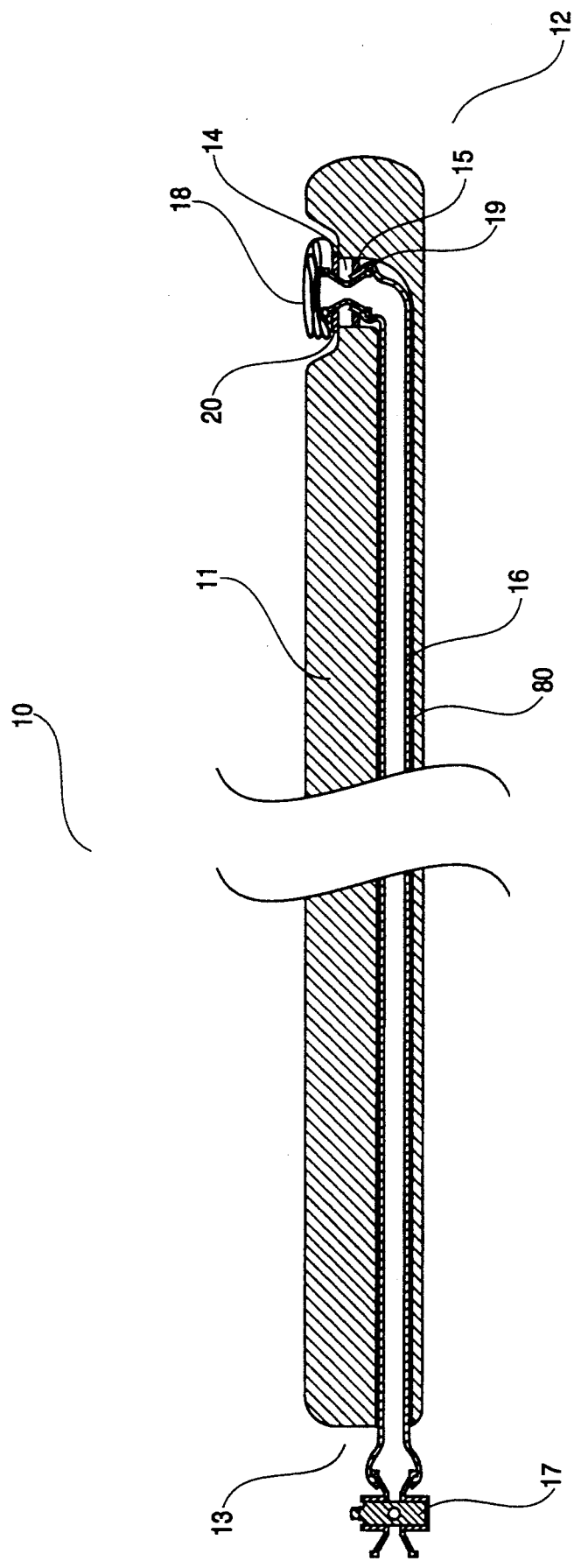
FIG. 1 shows a longitudinal cross-sectional view of one embodiment of the surgical retractor according to the present invention in which a disposable flexible tubing is threaded through a channel in a reusable shaft.

Referring now to FIG. 1, there is shown a longitudinal cross-sectional view of the surgical retractor according to the present invention. Laparoscopic surgical retractor 10 includes shaft 11 having a longitudinal axis, distal end 12, operative end 13, and interior channel 80 having openings at the distal and operative ends. Shaft opening 14 is positioned at distal end 12 of shaft 11. Within channel 80 is seal 15, which may be, for example, a rubber washer, which prevents the flow of gas or fluid from the exterior of retractor 10 into channel 80 when tubing 16 is located in channel 80. Insufflation tubing 16, which may consist of conventional clear polyethylene tubing, is threaded through channel 80 and extends from both the operative 13 and distal 12 ends of shaft 11. At the operative end, tubing 16 is connected to stopcock valve 17, which provides a means for introducing gas or fluid into tubing 16. With valve 17 in its closed position as shown, gas or fluid is not permitted to flow through tubing 80 into balloon 18. Connected to the opposite end of tubing 16 is balloon 18 which is an elastic skin capable of enclosing a variable volume cavity. The mouth of balloon 18 is sufficiently small to sealingly engage double flange connector 19. However, to provide additional protection from balloon 18 prematurely separating from flange connector 19, U clamp 20 is snugly fitted around the mouth of balloon and against connector 19. Double flange connector 19 is also connected to tubing 16.

It will be appreciated by those of skill in the art that balloon 18 may be connected to tubing 16 by other mechanisms. For example, threaded connectors, one attached to balloon 18 and its mate connected to tubing 16, or an adhesive may be used, or balloon 18 may be heat molded around insufflation tubing 16.

In this embodiment, shaft 11 may be made of, for example, stainless steel whose outer surface has been dulled to avoid intense reflection from shaft 11 while being viewed by an endoscope during the laparoscopic procedure. Thus, it's rigidity and weight may contribute to the retracting function as further described below. Furthermore, tubing 16, balloon 18, double flange connector 19 and stop cock 17 may all be constructed of disposable materials. This permits shaft 11 to be used for multiple laparoscopic surgical procedures, while replacing the other disposable materials for each procedure. Before use, the surgeon or a surgical assistant would assemble retractor 10 as shown. It will be appreciated by those of skill in the art that it is feasible for retractor 10 to be composed entirely of disposable materials and therefore only intended for a single use.

Figure 2:
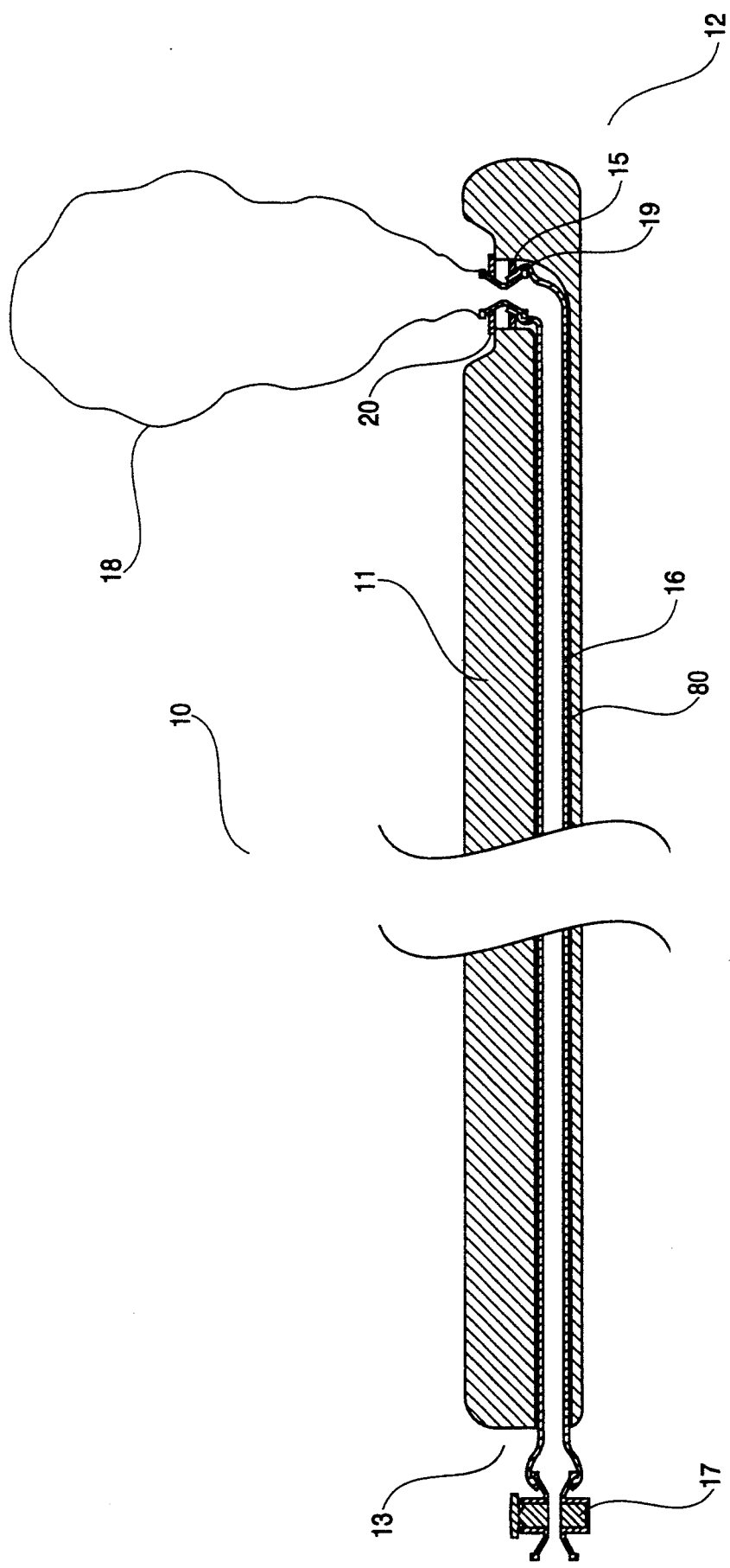
FIG. 2 shows a longitudinal cross-sectional view of the embodiment of FIG. 1 in which the balloon is partially inflated.
Figure 3:
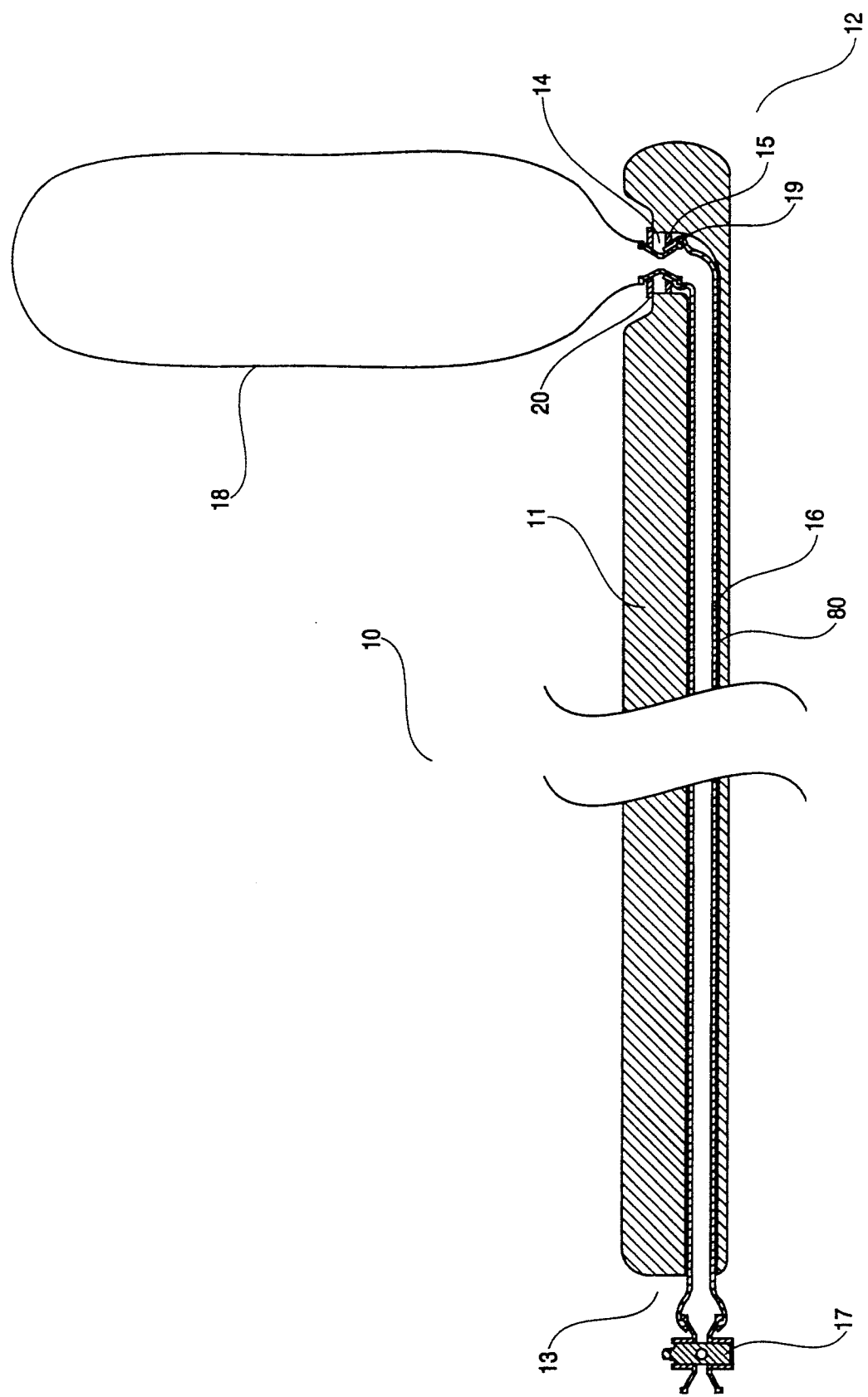
FIG. 3 shows a longitudinal cross-sectional view of the embodiment of FIG. 1 in which the balloon is fully inflated.

FIG. 2 shows a longitudinal cross-sectional view of the embodiment of FIG. 1 in which the balloon is partially inflated. By introducing gas, such as $CO_2$, or fluid, such as saline solution, to valve 17 and placing valve 17 in its open position as shown, balloon 18 begins to inflate. In FIG. 3, balloon 18 is fully inflated. It will be appreciated that balloon 18 may be selected and inflated to a size appropriate for the tissue to be retracted. In this embodiment, balloon 18 is substantially cylindrical in shape when inflated. It is also plausible that different shaped balloons may be used depending on the tissue to be retracted. Furthermore, more than one balloon may be connected to tubing 16 to vary the shape of the retractor and to widen the scope in which the retractor may be employed. In this embodiment, balloon 18 is approximately 6-7 centimeters in length and 2 centimeters in width, and shaft 11 is 18 to 24 centimeters in length, making surgical retractor 10 appropriate for use in retracting the transverse colon during a laparoscopic cholecystectomy.

Figure 4:
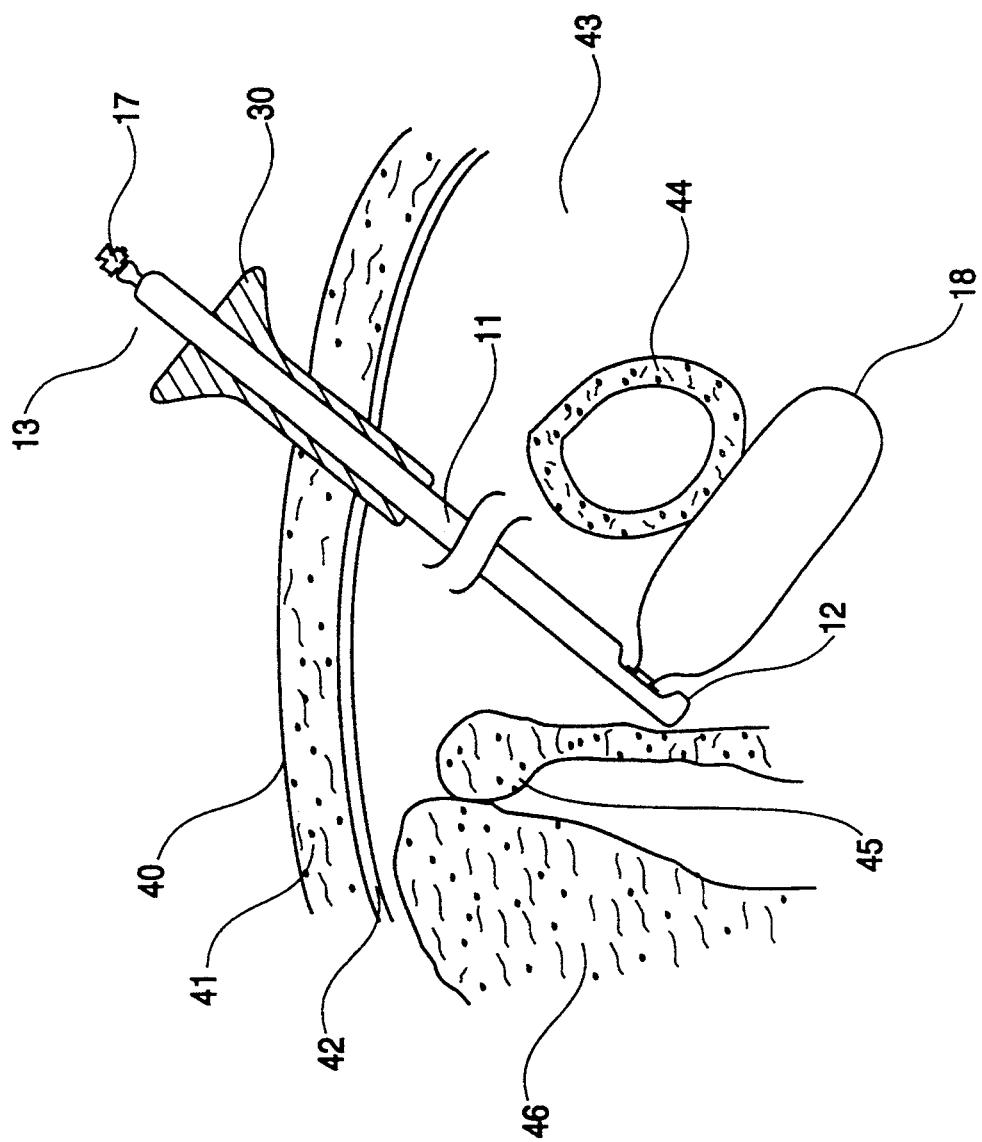
FIG. 4 shows a diagrammatic view of one embodiment of the method of the present invention in which tissue is retracted by the surgical retractor of FIG. 1 while the retractor remains within the cannula of a trocar.

FIG. 4 shows a diagrammatic view of one embodiment of the method of the present invention in which tissue is retracted by the surgical retractor of FIG. 1 while the retractor remains within the cannula of a trocar. Before balloon 18 is inflated, distal end 12 of surgical retractor 10 is inserted through trocar cannula 30 which extends through fascia 40, preperitoneal space 41 and peritoneum 42 into abdominal cavity 43 of the patient. Shaft 11 is of a diameter which is substantially the same as the inner diameter of trocar cannula 30 to prevent the escape of air from within the abdominal cavity through the cannula of trocar 30. Within abdominal cavity 43 are organs such as transverse colon 44, gall bladder 45 and liver 46. Once retractor 10 is inserted through cannula 30, it is positioned appropriately near the tissue or organ to be retracted, transverse colon 44 in this example. Retractor 10 may be moved or pivoted to position balloon 18 toward the optimal location for retraction. Gas or fluid is provided at valve 17 which is opened to thereby inflate balloon 18. Once balloon 18 is inflated, retractor 10 may be left within the cannula of trocar 30 to hold transverse colon 44 away from the surgical site.

Alternatively, the entire retractor may be pushed through trocar 30 so it resides entirely within the abdominal cavity. In this procedure, the weight of shaft 11 will be sufficient to hold retracting balloon 18 against the tissue to be retracting. This option will also allow trocar 30 to be used to introduce another retractor or surgical instrument to the surgical site.

Figure 5:
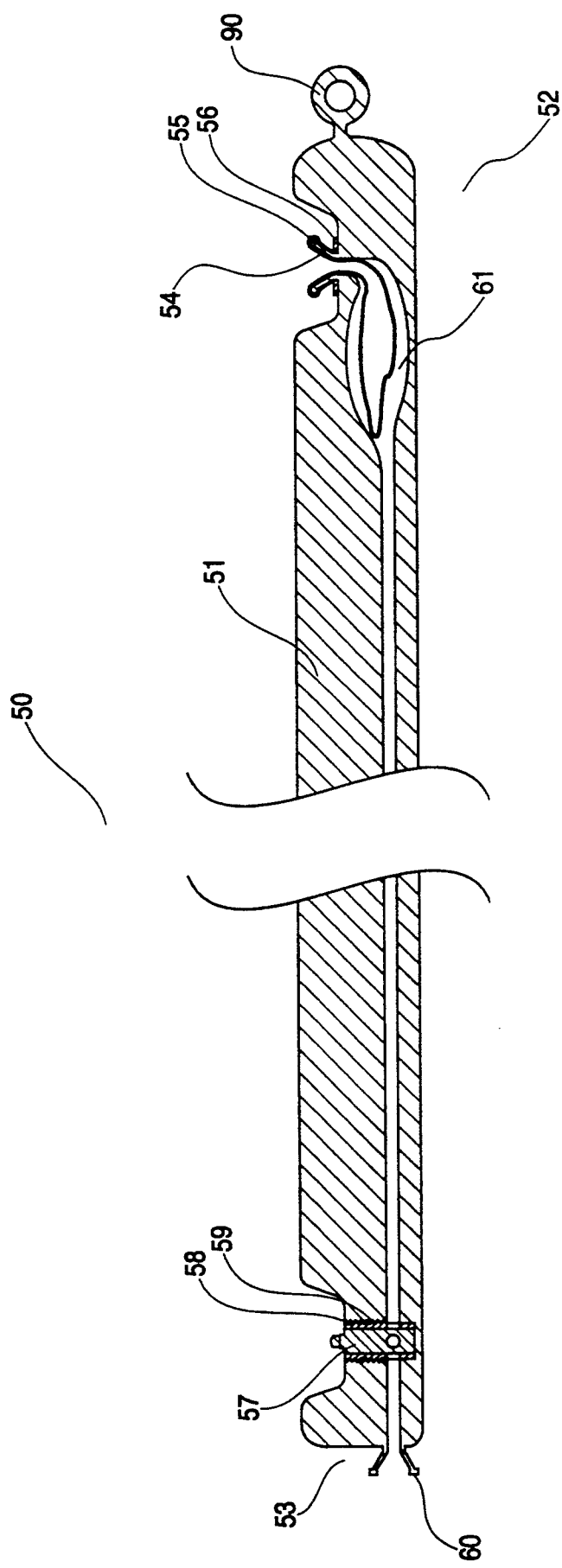
FIG. 5 shows a longitudinal cross-sectional view of a second embodiment of the surgical retractor according to the present invention in which the balloon is deflated and resides within a hollow cavity of the reusable shaft.

FIG. 5 shows a longitudinal cross-sectional view of a second embodiment of the surgical retractor according to the present invention in which the shaft includes an integral valve so that it may be entirely inserted through a trocar to reside entirely within an abdominal cavity. Surgical retractor 50 includes shaft 51 constructed of rigid material such as stainless steel. Of course, the outer surface of shaft 51 should be dulled so as to avoid the problem of unwanted reflection from retractor 50 while being viewed through an endoscope during a laparoscopic procedure. At distal end 52 of shaft 51 is distal flange 55 to which balloon 54 is connected by stretch fit and secured by U clamp 56. In this embodiment, when deflated, balloon 54 resides within hollow cavity 61 of shaft 51. At operative end 53 of shaft 51 is stop cock 57, a valve which provides a sealing means and serves as a means for introducing gas or fluid into shaft 51. In this embodiment, plastic stop cock valve 57 has threads 58 which are connected to shaft 51 at its threaded portion 59. Shaft 51 also includes flange 60 at operative end 53 to which a gas or fluid supply may be connected to introduce gas or fluid into shaft 51. In this embodiment, when gas or fluid is introduced into flange 60 and valve 57 is in its open position, balloon 54 is forced to out of cavity 61 and inflates in a manner similar to the embodiment shown in FIGS. 2 and 3.

It will be appreciated by those of skill in the art that balloon 54, clamp 56 and valve 57 may be made of disposable materials. In this manner, shaft 51 may be reused for multiple surgical procedures.

The embodiment of FIG. 5 also includes ring 90 disposed at distal end 52 of shaft 51. It will be appreciated that ring 90, or any other suitable grasping protrusion from distal end 52 of shaft 51, may be useful to the surgeon in positioning distal end 52 within the patient's abdominal cavity.

Figure 6B:
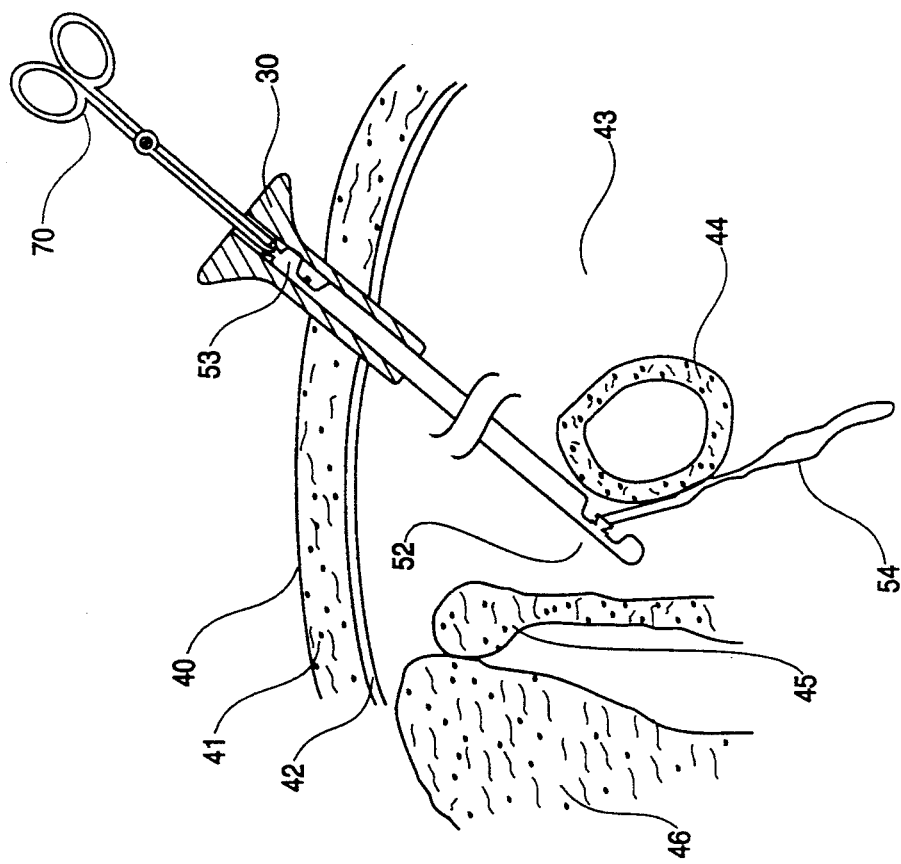
FIG. 6B shows a diagrammatic view of the embodiment of FIG. 6A in which the surgical retractor is in the process of being removed though the cannula of a trocar.
Figure 6A:
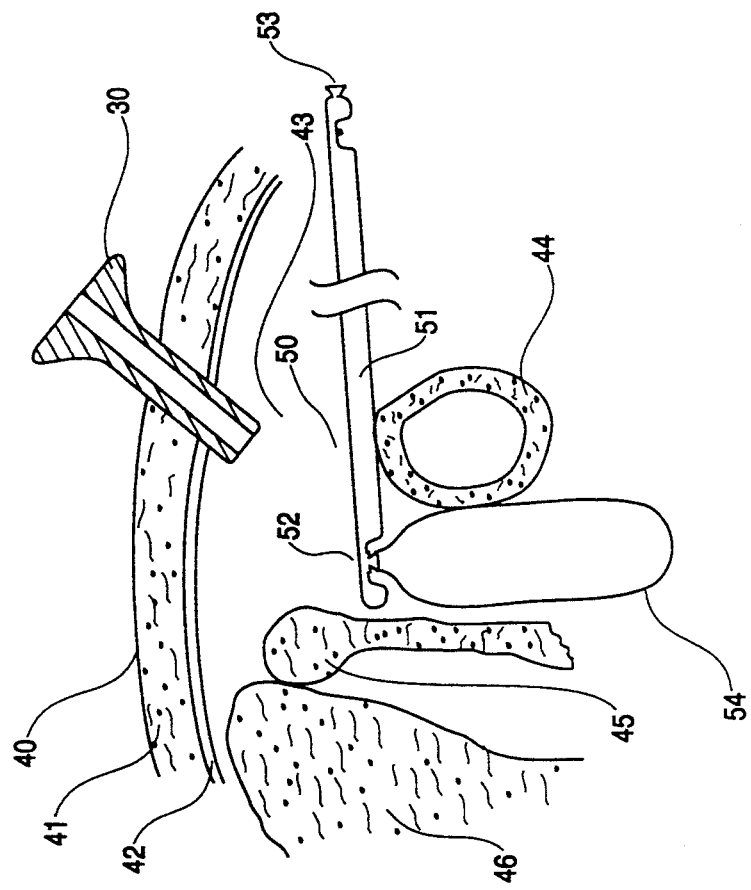
FIG. 6A shows a diagrammatic view of a second embodiment of the method of the present invention in which tissue is retracted by the surgical retractor of FIG. 5 which resides entirely within the abdominal cavity of the patient.

Referring now to FIG. 6A, there is shown a diagrammatic view of the second embodiment of the method of the present invention. In this embodiment, balloon 54 has been inflated by introducing gas or fluid through flange 60 with valve 57 in its open position, then valve 57 has been closed and the gas supply removed from flange 60. Finally, retractor 50 has been pushed entirely through the cannula of trocar 30 which is of substantially the same diameter as shaft 51. The surgeon then positions retractor 50 to reside entirely within abdominal cavity 43 such that both balloon 54 and shaft 51 hold transverse colon 44 away from the surgical site. It will be appreciated that the rigidity and substantial weight of shaft 51 results in the proper retraction of transverse colon 44 without requiring retractor 50 to remain within trocar cannula 30. Thus, trocar cannula 30 may be used for other surgical devices including other retractors.

FIG. 6B shows a diagrammatic view of the embodiment of FIG. 6A in which the surgical retractor is in the process of being removed though cannula 30 of a trocar. To remove retractor 50, the surgeon uses a tool such as forceps 70 to grasp operative end 53 of shaft 51 and to pull shaft 51 from within abdominal cavity 43 to outside the patient's abdomen. Of course, before retractor 54 is removed through the trocar cannula, balloon 54 must be deflated which may be accomplished by puncturing balloon 54 or by opening valve 57.

Figure 7:
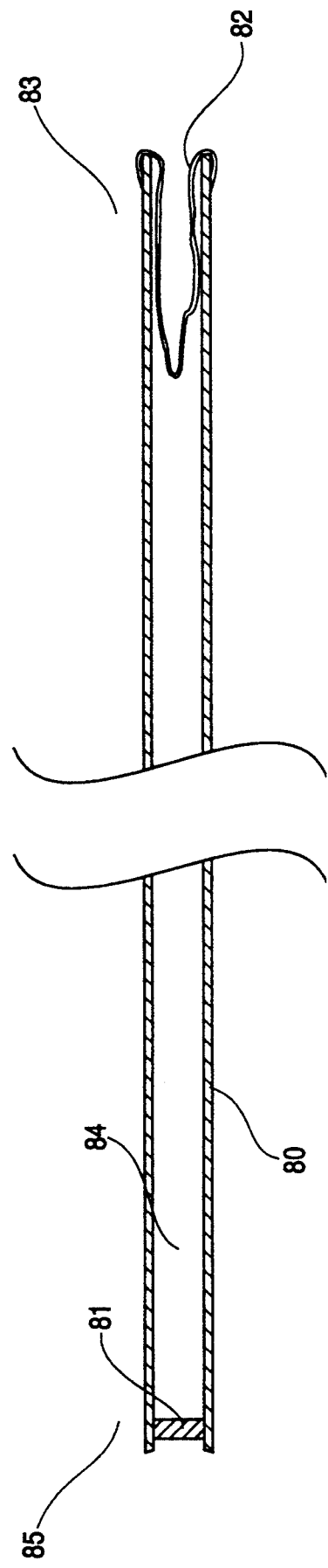
FIG. 7 shows an alternate embodiment of the invention in which the shaft is disposable and includes a puncturable self-sealing seal.

FIG. 7 shows a third embodiment of the invention in which shaft 80 has a permanently fitted balloon 82 heat sealed to its distal end 83. Operative end 85 of shaft 80 includes a rubber sealing plug 81, which seals interior channel 84. This embodiment of the invention may be entirely disposable. To use this embodiment, distal end 83 is placed through a trocar so that it resides within the abdominal cavity, but while operative end 85 still extends from the exterior of the body. An insufflation needle may be used to puncture seal 81 and thereby inflate balloon 82 with gas or fluid. The needle is then withdrawn, and the self-sealing nature of plug 81 prevents the escape of the gas or fluid from the filled balloon. Shaft 80 may then be manipulated to force balloon 82 to the appropriate tissue-retracting position. Leaving shaft 80 inserted in the trocar may assist in holding balloon 82 in place. Alternatively, shaft 80 may be pushed entirely through the trocar as described above for the second embodiment of the invention.

It will be further appreciated that the surgical retractor disclosed herein provides for laparoscopic surgery a device which is similar in function to a retractor that is used in conventional surgery with open incisions. In addition, the retractor may be inflated to different volumes to match the tissue to be retracted. Because the inflatable retractor distributes its forces over a broad area, the risk of trauma to retracted tissue is reduced. Moreover, multiple retractors may be inserted into a body cavity through a single trocar, thereby eliminating the need for a separate trocar for each retractor.

I claim:

1. A method of retracting tissue during laparoscopic surgery comprising the steps of:
    making a first incision into an abdominal cavity,
    inflating the abdominal cavity by providing a gas through the first incision, the first incision being substantially sealed but for the provision of gas therethrough,
    making a laparoscopic incision into the abdominal cavity,
    placing a laparoscopic trocar cannula into the laparoscopic incision,
    providing a retractor, the retractor comprising
        an elastic skin enclosing a variable volume cavity, and
        seal means in communication with the cavity of the elastic skin to prevent deflation of the skin after it has been inflated,
    inserting into the abdominal cavity through the trocar cannula substantially the entire retractor including the seal means,
    positioning the elastic skin against tissue within the abdominal cavity to be retracted while the abdominal cavity remains inflated and sealed,
    inflating the elastic skin such that the tissue is thereby retracted,
    deflating the elastic skin,
    removing the retractor from the abdominal cavity through the trocar cannula, and
    deflating the abdominal cavity.

2. The method of retracting tissue of claim 1 wherein the retractor further elongate a shaft insertable through the laparoscopic trocar cannula, the shaft having a distal end an operative end, and an interior channel having ends terminating at the distal and operative ends, the shaft comprising inflation means for inflating the elastic skin, and the elastic skin located proximate the distal end of the shaft, such that, prior to the inflation of the elastic skin, the inflation means extends through the trocar cannula to the exterior of the abdomen, the method further comprising, prior to the step of deflating the elastic skin the step of:
    pushing the inflation means completely through the laparoscopic trocar and into the abdominal cavity.

3. The method of retracting tissue of claim 2 further comprising, prior to the step of deflating the elastic skin the step of:
    positioning the inflation means to hold the retractor in place.

* * * * *